(12) United States Patent
Reeve et al.

(10) Patent No.: US 6,399,364 B1
(45) Date of Patent: Jun. 4, 2002

(54) SEQUENCING BY HYBRIDIZATION

(75) Inventors: Michael Alan Reeve, Oxfordshire; Terek Schwarz, Greater London, both of (GB)

(73) Assignee: Amersham Biosciences UK Limited, Bucks (GB)

(*) Notice: Subject to any disclaimer, the term of this patent is extended or adjusted under 35 U.S.C. 154(b) by 0 days.

(21) Appl. No.: 09/646,530

(22) PCT Filed: Mar. 19, 1999

(86) PCT No.: PCT/GB99/00875

§ 371 (c)(1),
(2), (4) Date: Nov. 9, 2000

(87) PCT Pub. No.: WO99/47706

PCT Pub. Date: Sep. 23, 1999

(30) Foreign Application Priority Data

Mar. 19, 1998 (GB) .............................................. 9805918

(51) Int. Cl.[7] .............................. C12M 1/34; C12Q 1/68; C12P 19/34; G01N 33/00; C07H 21/04
(52) U.S. Cl. ........................ 435/287.2; 435/6; 435/91.1; 435/287.1; 436/94; 536/24.3
(58) Field of Search ......................... 435/6, 91.1, 91.2, 435/183, 283.1, 287.1, 287.2; 436/94, 501; 536/23.1, 24.3, 24.33, 25.3

(56) References Cited

U.S. PATENT DOCUMENTS 5,641,630 A * 6/1997 Snitman et al. ................. 435/6
5,683,881 A 11/1997 Skiema
5,800,999 A * 9/1998 Bronstein et al. ............... 435/6

FOREIGN PATENT DOCUMENTS

WO 95 09248 A 4/1995

OTHER PUBLICATIONS

Chou et al., Affinity methods for purification of DNA sequencing reaction products for mass spectrometric analysis. Rapid Commun. Mass Spectro. 10, 1410–1414, 1996.*
Yershov et al., DNA analysis and diagnostics on oligonucleotide microchip. Proc. Natl. Acad. Sci. USA, 93, 4913–4918, 1996.*
K.R. Khrapko et al., "A Method for DNA Sequencing by Hybridisation with Oligonucleotide Matrix", DNA Sequence–I DNA Sequencing and Mapping, vol. 1, 1991, pp. 375–388.

* cited by examiner

*Primary Examiner*—Ethan C. Whisenant
*Assistant Examiner*—Frank Lu
(74) *Attorney, Agent, or Firm*—Wenderoth, Lind & Ponack, L.L.P.

(57) ABSTRACT

A method of analysing a nucleic acid is disclosed which involves the use of a mixture of labelled oligonucleotides in solution and an array of immobilized oligonucleotides. The target nucleic acid is incubated with the mixture of labelled oligonucleotides. Those labelled oligonucleotides which hybridize are recovered and incubated with the array of immobilized oligonucleotides. Sequence information is obtained by observing the location of the label on the array. The method is particularly suitable for determining differences between nucleic acids.

13 Claims, No Drawings

SEQUENCE LISTING

<160> NUMBER OF SEQ ID NOS: 4

<210> SEQ ID NO 1
<211> LENGTH: 82
<212> TYPE: DNA
<213> ORGANISM: Homo sapiens

<400> SEQUENCE: 1
gttttcccag tcacgacgac catggtgcac ctgactcctg aggagaagtc t gccgttact       60 gccatggtca tagctgtttc ct                                                82

<210> SEQ ID NO 2
<211> LENGTH: 82
<212> TYPE: DNA
<213> ORGANISM: Homo sapiens

<400> SEQUENCE: 2
gttttcccag tcacgacgac catggtgcac ctgactcctg tggagaagtc t gccgttact       60 gccatggtca tagctgtttc ct                                                82

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: DNA PRIMER

<400> SEQUENCE: 3
gttttcccag tcacgacg                                                     18

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: DNA PRIMER

<400> SEQUENCE: 4
aggaaacagc tatgaccat                                                    19

SEQUENCING BY HYBRIDIZATION

This is a 371 application of PCT/GB99/00875 filed Mar. 19, 1999.

BACKGROUND OF THE INVENTION

1. Field of the Invention

The present invention is related to the sequencing of nucleic acids by hybridization. line 5, replace the heading with the following new heading 2. Description of the Related Art There are currently three formats for sequencing by hybridisation (SBH).

Format 1 SBH [1] attaches the nucleic acid to be analysed to a solid support and then sequentially hybridises labelled oligonucleotides. Format 2 SBH [2] attaches an array of positionally encoded oligonucleotides to a solid support and then hybridises the labelled nucleic acid to be analysed to the array. Format 3 SBH [3] attaches an array of positionally encoded oligonucleotides to a solid support and then hybridises the nucleic acid to be analysed to the array in the presence of is labelled oligonucleotides in free solution. A ligation reaction is then used in order to join the two oligonucleotides, giving greater specificity and information.

Format 1 SBH has been shown to work with short oligonucleotides [4]. 8 mers and even shorter oligonucleotides have been successfully employed [5]. Format 2 SBH requires the use of much longer oligonucleotides for success. 11 mer probes, or longer, are generally required. 20 mers are the norm [6], making the use of generic arrays of all N mers out of the question with current technology (an array of all 20 mers with the smallest pixels currently imaginable would be prohibitively large).

A difficulty with performing format 2 SBH arises because target nucleic acids often have secondary structure which sterically hinders some parts of the target from hybridising with oligonucleotides immobilised in an array. To overcome this problem it has been proposed to chop the target nucleic acid into shorter segments, e.g. of length comparable to the immobilised oligonucleotides. In practice such chopping has proved difficult to achieve in a reliable and uniform manner. The present invention can be seen as providing an indirect way of achieving the same effect. The invention permits the advantages of both format 1 and format 2 SBH to be combined in the same method. In particular, the use of a format 2 positionally encoded array of all N mers or a subset thereof is made possible with arrayed oligonucleotides of length less than 11 mers. This method allows the rapid and facile characterisation of sequence differences between two or more nucleic acid species. The method may be used in order to determine the existence or otherwise of point mutational differences between one or more test nucleic acids and a reference nucleic acid. The method may also be used in order to characterise sequence differences arising from either small deletions or insertions.

SUMMARY OF THE INVENTION

In one aspect the invention provides a method of analysing a target nucleic acid by the use of a mixture of labelled oligonucleotides in solution and an array of immobilised oligonucleotides, which method comprises the steps of:

a) incubating under hybridisation conditions the target nucleic acid with the mixture of labelled oligonucleotides.

b) recovering those labelled oligonucleotides that hybridised in a) with the target nucleic acid, c) incubating under hybridisation conditions the recovered labelled oligonucleotides from b) with the array of immobilised oligonucleotides, d) observing distribution of the labelled oligonucleotides on the array and using the information to analyse the target nucleic acid.

In another aspect the invention provides a method of determining differences between a target nucleic acid and a reference nucleic acid, by the use of a first mixture of oligonucleotides in solution labelled with a first label, a corresponding mixture of oligonucleotides in solution labelled with a second label distinguishable from the first label, and an array of immobilised oligonucleotides, which method comprises the steps of:

a) incubating under hybridisation conditions the target nucleic acid with the first mixture of labelled oligonucleotides; and incubating under hybridisation conditions the reference nucleic acid with the second mixture of labelled oligonucleotides, b) recovering a mixture of those first labelled oligonucleotides and those second labelled oligonucleotides that hybridised in a) with the target nucleic acid or the reference nucleic acid, c) incubating under hybridisation conditions the recovered mixture of first labelled oligonucleotides and of second labelled oligonucleotides from b) with the array of immobilised oligonucleotides, d) observing distribution of first labelled oligonucleotides and of second labelled oligonucleotides on the array and using the information to determine differences between the target nucleic acid and the reference nucleic acid.

DESCRIPTION OF THE PREFERRED EMBODIMENTS

Preparation of Single Stranded Nucleic Acid

The target nucleic acids may be DNA, RNA, PNA [7], other nucleic acid mimetics or mixtures thereof. They may be single stranded or double stranded; linear, circular, relaxed or supercoiled. They may be of eukaryotic, prokaryotic or viral or archeabacterial origin and may range in size from oligomers to whole genomes.

The target nucleic acids are rendered single stranded. The most preferable method is to amplify the region of interest by PCR [8] and then capture one of the amplified strands using a solid support. Many methods will be obvious to those skilled in the art. The use of a biotinylated PCR primer followed by capture with streptavidin coated magnetic beads [9] is a preferred embodiment.

The PCR may be carried out either by using conventional dNTPs or dNTP analogues that impart altered properties to the PCR product—such as reduced intramolecular secondary structure and thus improved short oligonucleotide access to PCR product in single stranded form. Example nucleotide analogues include: dITP, 7-deaza-dGTP, 7-deaza-dATP, 7-deaza-dITP, 5-hydroxymethyl-dUTP and 4-methyl-dCTP—either singly and in combination. Many other analogues will be obvious to those skilled in the art. Some of these analogues may require the use of lower PCR annealing temperatures and/or longer PCR extension times for optimal incorporation.

The method of the invention involves use of a mixture of labelled oligonucleotides in solution. This is preferably a mixture of all or a subset of N mers where N is from 5 to 10, preferably 8 or 9. The labelling moieties may be detected by means of fluorescence (emission, lifetime or polarisation), absorption, colour, chemiluminescence, enzymatic activity, radioactive emission, mass spectroscopy or refractive index effects (e.g. surface plasmon resonance).

The N mers in solution may be DNA, RNA, PNA, other nucleic acid mimetics or mixtures thereof. They may be single stranded or partially double stranded. The N mers may also contain bases such as 5-nitroindole, 3-nitropyrrole or inosine that pair with all four usual DNA bases—improving the hybridisation properties of the N mers without increasing the nucleic acid sequence complexity. The N mers may likewise contain bases such as 2-aminopurine and 5-methylcytosine that again improve the hybridisation properties without increasing the nucleic acid sequence complexity.

Structures that can only (or preferentially) form A helices are of particular interest as conditions may be found (e.g. R-loop conditions) where the N mer/PCR product complexes are more stable than the internal secondary structure within the PCR product.

The N mers could also be molecular beacon [10] type 'panhandle' structures with stems comprising 5-nitroindole, 3-nitropyrrole, inosine, isodC:isodG [11], dk:dX [12] or dk:dp [13] hairpins. Other such structures will be obvious to those skilled in the art.

The method of the invention also involves use of an array of immobilised oligonucleotides. Each oligonucleotide is immobilised at a spaced location on a surface of a support. The array is preferably of all possible N mer sequences or a subset thereof where N is preferably from 5 to 10, particularly 8 or 9.

The array elements may be DNA, RNA, PNA, other nucleic acid mimetics or mixtures thereof. They may be single stranded or partially double stranded. The array elements may also contain bases such as 5-nitroindole, 3-nitropyrrole or inosine that pair with all four DNA bases—improving the hybridisation properties of the array without increasing its nucleic acid sequence complexity. The array elements may likewise contain bases such as 2-aminopurine and 5-methylcytosine that again improve the hybridisation properties of the array without increasing its nucleic acid sequence complexity.

Arrays may be employed on glass, plastic, silicon, supported membrane and supported gel substrates. A given substrate may have one or more test site arrays for use with the invention.

In step a) of the method, the target nucleic acid is incubated under hybridisation conditions with the mixture of labelled oligonucleotides. In step b), those labelled oligonucleotides that hybridised in a) with the target oligonucleotide are recovered. Where the target nucleic acid has been immobilised on magnetic beads as discussed above, the captured oligonucleotides may readily be recovered by denaturation and removal of the magnetic beads In a preferred aspect, the method of the invention may be performed to determine differences between a target nucleic acid and a reference nucleic acid. In this case, the reference nucleic acid is incubated under hybridisation conditions with a second mixture of labelled oligonucleotides, and those members of that mixture that hybridised with the reference nucleic acid are recovered. The first mixture of labelled oligonucleotides in solution is distinguishable from the second mixture of labelled oligonucleotides in solution. For example, the labels used may be fluorescent dyes having different fluorescence characteristics. The labels are herein called label 1 and label 2. Preferably the two sets of captured oligonucleotides are mixed.

In step c) the recovered mixture of labelled oligonucleotides is incubated under hybridisation conditions with the array of immobilised oligonucleotides.

Upon hybridisation to the array, captured oligonucleotides in the test and reference nucleic acids of N bases complementary to array sequences will display the normal ratio of label 1 to label 2 upon detection where the test and reference nucleic acid have the same sequence—i.e. in the majority of cases.

Upon hybridisation to the array, captured oligonucleotides in the test and reference nucleic acids of N bases complementary to array sequences will display an altered normal ratio of label 1 to label 2 upon detection where the test and reference nucleic acid have different sequence—i.e. in the vicinity of a mutation.

Difference Characterisation

By observing the sequences of array elements where the label 1 to label 2 ratio is different from the majority of hybridisation events and by observing which of the two labelled moieties dominates at each such complementary array element (of known sequence), one may deduce the sequence at and around any difference between the two nucleic acid species. In the simple case of a point mutational difference between the test and reference nucleic acid with an array of all possible N-mers, a region of 2N−1 bases will be characterised (the reference/mutated base and the N−1 bases to either side of this).

Advantages of the Current Invention

A particular problem that is overcome in this approach where part of the amplified single stranded region of interest has significant internal secondary structure. This situation will deny access from short oligonucleotides in solution (or as part of a positionally encoded array on a solid support). It is essentially for this reason that success has not been achieved for format 2 SBH with arrayed oligonucleotides shorter than 11 mers (arrays of 20 mers are generally used). In this invention, nucleotide analogues may be used—either in the PCR reaction or in the solution oligonucleotides or in the arrayed oligonucleotides—in order to circumvent problems with PCR product secondary structure.

This method has the advantage that by detecting perturbations in the ratio between the labelling moieties upon detection, all hybridisation events are internally controlled for their absolute hybridisation intensities—a significant improvement over other SBH methods. Not only is information given that a difference exists between the two nucleic acid species but also the exact nature of the difference and the local sequence around this difference can be determined.

If four colour detection is implemented, the mutational event could be sequenced on both strands simultaneously—greatly improving the accuracy of an already very information—rich method.

The method does not use enzymes for the recognition of sequence differences. The method thus provides a more robust and reliable way to characterise nucleic acid sequence differences.

In addition to the above, a single array of, for example, all possible N-mers or a subset thereof, can be employed for the analysis of any nucleic acid system. Unlike other methods for sequence characterisation with arrays [6], a distinct sequence array does not need to be fabricated anew for every nucleic acid system that is to be characterised.

Unlike methods such as SSCP [14], where the optimal size for a PCR product is around 200 bp, this method allows the user to 'walk' along a genomic region of interest in much larger steps—1–10 kb fragments would probably be about optimum for this method.

This method allows for highly parallel analysis where the shorter labelled oligonucleotides allow better mismatch discrimination. Repeated cycles of N mer capture and denaturation can be used to improve the final detection signal. Optimal chemical intermediates can selectively overcome, secondary structure. Incomplete arrays of (optimised) longer probes could be used with appropriate sequence reconstruction algorithms. Solution hybridisation to long probes and oligonucleotide hybridisation to the array should also be faster.

The present invention will now be illustrated in more detail in the Example below. However, it is important to note that the following Example represents only a specific embodiment of the present invention. Other embodiments are also possible and encompassed by the claims. Thus, the following Example should not be construed to limit the spirit and scope of the claims.

EXAMPLE

Step 1

All oligonucleotides were synthesised by MWG Biotech Ltd, Milton Keynes, UK).

The two target sequences comprise 45 bases spanning the human HbA and HbS beta globin gene sequences respectively. These two sequences differ at a single base positon resulting in a change in codon 6 from GAG to GTG. The resulting amino acid substitution from Glu to Val in the beta globin gene is responsible for sickle cell disease. Octamer oligonucleotides corresponding to the region immediately surrounding the mutation, sequences shared by both the HbA and HbS, and sequences mismatched by one base to one or both templates were synthesised with a terminal phosphorothioate, attached to the oligonucleotide via a $(C_{18})_3$ linker, for spotting in an array. Octamers complementary to HbA (Cy3 labelled) and HbS (Cy5 labelled) were synthesised for the solution hybridisation. The sequences are set out below.

Step 2

Synthetic template (0.1 uM HbS or HbA) was subjected to a polymerase chain reaction (PCR) in the presence of 0.4 uM each of the forward and biotinylated reverse sequencing primers, 250 uM deoxyribonucleotides (Amersham Pharmacia Biotech), 1×PCR buffer (Amersham-Pharmacia Biotech) and 2Units of Taq DNA polymerase (Amersham-Pharmacia Biotech) in a total volume of 100 µl. The thermal cycling was carried out on an MJ Research DNA engine (MJ Research inc. Watertown Mass. USA) for 25 cycles of; 95° C. 1 min; 50° C. 30 sec; 72° C. 30 sec.

Step 3

Streptavidin coated paramagnetic beads (Advanced Biotechnologies Ltd. UK) were magnetically captured in a brown 1.5 ml Eppendorff tube (5 mg/tube), then washed twice in 5×SSC, 5% TWEEN-20 (polyoxyethylene (20) sorbitan monolaurate). Following the final capture, the beads were resuspended in 0.5 ml of 5×SSC, 5% TWEEN-20 (polyoxyethylene (20) sorbitan monolaurate). A 100 µl aliquot of PCR product from Step 2 was added to an equal volume of the bead suspension. The mixture was incubated at room temperature for 2 h, with the beads maintained in suspension by continuous mixing.

Following template binding, the beads were washed three times for 10 min. with 5×SSC, 5% TWEEN-20 (polyoxyethylene (20) sorbitan monolaurate) at room temperature. The beads were resuspended in 100 µl of 0.05 M NaOH, 1% (v/v) TWEEN-20 (polyoxyethylene (20) sorbitan monolaurate) and allowed to stand for 2 min. The beads were then captured and resuspended in a second 100 µl aliquot of 0.05 M NaOH, 1% (v/v) TWEEN-20 (polyoxyethylene (20) sorbitan monolaurate). After a further 2 min. at room temperature, the beads were captured and the denaturing solution aspirated. The single stranded template bound to the beads was washed four times for 10 min. with 5×SSC, 5% TWEEN-20 (polyoxyethylene (20) sorbitan monolaurate). The beads were finally resuspended in 100 µl 5×SSC, 5% TWEEN-20 (polyoxyethylene (20) sorbitan monolaurate).

Step 4

Hybridisation of the oligonucleotide probe mixture to bead-bound single stranded template was performed overnight at 4° C. A 50 µl volume of beads was magnetically captured and the supernatant aspirated. To the captured beads 125 µl of 10×SSC, 10%(v/v) TWEEN-20 (polyoxyethylene (20) sorbitan monolaurate) were added and mixed with 125 µl of an oligonucleotide probe mixture, in water, containing 0.4 µM each labelled oligonucleotide. The beads were maintained in suspension by continuous mixing on a rolling mixer.

Following hybridisation, the beads were washed 3 times at 4° C. for 20 min. in 5×SSC, 5% TWEEN-20 (polyoxyethylene (20) sorbitan monolaurate). After the final wash, the beads were resuspended in 20 µl of water and the suspension heated to 90° C. for 3 min. The tubes were then quickly immersed in ice water and the beads separated on an ice-cold capture magnet. An aliquot of the eluted probe was mixed with an equal volume of 10×SSC, 10% TWEEN-20 (polyoxyethylene (20) sorbitan monolaurate) and used directly in a hybridisation on glass slides.

Step 5

Untreated glass slides (Erie Scientific, Portsmouth N.H. USA, Cat No. 2959F*) were soaked in 5%(v/v) (3-mercaptopropyl)trimethoxysiiane (Aldrich Chemical Co., Poole, Dorset, UK) in dry toluene for 6 hours. The slides were washed with dry toluene followed by ethanol. The slides were then soaked overnight in a 6.66 g/l isopropanol solution of 2,2'-dipyridyl disulfide (Sigma Chem. Co. UK). The slides were finally washed three times with isopropanol and air-dried.

Step 6

The microtitre plates, containing oligonucleotides to be arrayed, were prepared by mixing in each well 5 µl of an oligonucleotide solution (20 pmol/l), 10 µl of 50%(v/v) aqueous ethyleneglycol and 5 l of imidazole buffer pH4. Glass slides prepared in Step 5 were spotted with the oligonucleotide solutions using a Molecular Dynamics spotter set in normal mode at a humidity of 45–47% and a temperature of 20° C. Once spotted, the slides were kept over night at room temperature in a humidified chamber. The slides were then washed with water, rinsed with isopropanol and allowed to dry.

Step 7

Probe solutions (10 µl aliquots) from Step 4 were applied to the arrays prepared in Step 6 and covered with a coverslip. The slides, kept above water in a sealed box, were heated to 60° C. in an Amersham Pharmacia Biotech hybridisation oven, kept at this temperature for 1 hour, then cooled in the oven to room temperature over a period of 3 hours, followed by 2 hours at room temperature. The slides were washed twice for 3 minutes at 4° C. with 5×SSC, 5% TWEEN-20 (polyoxyethylene (20) sorbitan monolaurate). The washed slides were scanned for the Cy3 and Cy5 fluorescence signals using a Molecular Dynamics generation III microarray scanner with default settings, 695V for the green laser, 750V for the red laser. The scans were analysed using Molecular Dynamics' Image Quant and Microsoft Excel software.

HbS template was subjected to a hybridisation described in Step 4 and the resulting eluate of oligonucleotides was hybridised to the array of octamers described in Step 7. The resulting hybridisation pattern showed that all eight octamers tiled across the HbS polymorphism had hybridised and produced a signal. Hybridisation signal with both Cy5 and Cy3 was also observed for the oligonucleotides that are common to both templates. Negligible signal was observed for any of the mismatched oligonucleotides, thus demonstrating the capture and hybridisation of template specific oligonucleotides. A number of array elements failed to produce a signal when hybridisation was performed directly with the Cy3 and Cy5 oligonucleotides and were exluded from the analysis as void elements.

HbA Template Hybridised with Cy5 and Cy3 Labelled Oligonucleotide Mixture

The HbA template was subjected to analysis as described for the HbS template above. HbA specific Cy3 fluorescece was observed on the array. Five of the Eight HbA specific elements of the array gave a positive signal. The negative elements that would have been expected to give a signal when hybridised to a matched probe were also negative when the fluorescent oligonucleotides were added directly to the array. This finding confirmed that the absence of signal at these points was the result of spot failure, rather than absence of the appropriate fluorescent oligonucleotide. Functional array elements representing shared sequence showed up with both Cy3 and Cy5 fluorscence signals. HbS specific array elements and mismatched oligonucleotides gave either faint signal or no signal at all HbA and HbS Templates Hybridised with Cy5 and Cy3 Labelled Oligonucleotides When both HbA and HbS templates were present, all Functional elements of the array gave a fluorescent signal for matched oligonucleotides, with the HbS and HbA elements of the array producing Cy5 and Cy3 signals respectively. Common sequences produced a signal with both Cy3 and Cy5 oligonucleotides. Mismatched oligonucleotides showed only faint signal or no signal in both Cy3 and Cy5 channels.

Templates

```
HbA SEQUENCE
GTTTTCCCAGTCACGACG
ACCATGGTGCACCTGACTCCT [GAG] GAGA
AGTCTGCCGTTACTGCCATGGTCATAG
CTGTTTCCT    (SEQ ID No.1)

HbS SEQUENCE
GTTTTCCCAGTCACGACG
ACCATGGTGCACCTGACTCCT [GTG] GAGA
AGTCTGCCGTTACTGCCATGGTCATAG
CTGTTTCCT    (SEQ ID No.2)
```

Underlined sequences represent
a primer binding sequence, or its
complement, that has been
appended to the Hb sequence.
The boxed nucleotides in bold
type highlight the single base
polymorphism of codon6.

Forward primer

GTT TTC CCA GTC ACG ACG (SEQ ID No.3)

Reverse primer

5'Biotin-AGG AAA CAG CTA TGA CCA T
(SEQ ID No.4)

Reverse sequencing primer is
biotinylated at the 5' end to
permit capture on streptavidin
coated surfaces.

```
5'-p(s)-XXX-CCACAGGA-3'
5'-p(s)-XXX-TCCACAGG-3'
5'-p(s)-XXX-CTCCACAG-3'
5'-p(s)-XXX-TCTCCACA-3'
5'-p(s)-XXX-TTCTCCAC-3'
5'-p(s)-XXX-CTTCTCCA-3'
```

Oligonucleotides common to both templates

```
5'-p(s)-XXX-CGTCGTGA-3'
5'-p(s)-XXX-GTCGTGAC-3'
5'-p(s)-XXX-TCGTGACT-3'
5'-p(s)-XXX-CGTGACTG-3'
5'-p(s)-XXX-GTGACTGG-3'
5'-p(s)-XXX-ATGACCAT-3'
5'-p(s)-XXX-TATGACCA-3'
5'-p(s)-XXX-CTATGACC-3'
5'-p(s)-XXX-ACTATGAC-3'
5'-p(s)-XXX-CACTATGA-3'
```

Oligonucleotides with one base mismatch to
either HbA, HbS, or both.

```
5'-p(s)-XXX-CTCATCAG-3'
5'-p(s)-XXX-CTCGTCAG-3'
5'-p(s)-XXX-CTCTTCAG-3'
5'-p(s)-XXX-CTCAACAG-3'
5'-p(s)-XXX-CTCGACAG-3'
5'-p(s)-XXX-CTCTACAG-3'
5'-p(s)-XXX-TCGAGACT-3'
5'-p(s)-XXX-TCGCGACT-3'
5'-p(s)-XXX-TCGGGACT-3'
5'-p(s)-XXX-CTAAGACC-3'
5'-p(s)-XXX-CTACGACC-3'
5'-p(s)-XXX-CTAGGACC-3'
```

Oligonucleotides for preparing the array

P(s) = phosporothioate, X = C18 linker.

HbA specific oligonucleotides

5'-p(s)-XXX-TCAGGAGT-3'
5'-p(s)-XXX-CTCAGGAG-3'
5'-p(s)-XXX-CCTCAGGA-3'
5'-p(s)-XXX-TCCTCAGG-3'
5'-p(s)-XXX-CTCCTCAG-3'
5'-p(s)-XXX-TCTCCTCA-3'
5'-p(s)-XXX-TTCTCCTC-3'
5'-p(s)-XXX-CTTCTCCT-3'

HbS specific oligonucleotides

5'-p(s)-XXX-ACAGGAGT-3'
5'-p(s)-XXX-CACAGGAG-3'

Fluorescently labelled capture oligonuclotides.

5'Cy3-ACTCCTGA3'
5'Cy3-CTCCTGAG3'
5'Cy3-TCCTGAGG3'
5'Cy3-CCTGAGGA3'
5'Cy3-CTGAGGAG3'
5'Cy3-TGAGGAGA3'
5'Cy3-GAGGAGAA3'
5'Cy3-AGGAGAAG3'
5'Cy3-TCACGACG3'
5'Cy3-GTCACGAC3'
5'Cy3-AGTCACGA3'
5'Cy3-CAGTCACG3'
5'Cy3-CCAGTCAC3'
5'Cy3-ATGGTCAT3'
5'Cy3-TGGTCATA3'
5'Cy3-GGTCATAG3'
5'Cy3-GTCATAGCT3'
5'Cy3-TCATAGCTG3'

What is claimed is:

1. A method of analysing a target nucleic acid by the use of a mixture of labelled oligonucleotides in solution and an array of immobilised oligonucleotides, which method comprises the steps of:

a) incubating under hybridisation conditions the target nucleic acid with the mixture of labelled oligonucleotides, b) dissociating and recovering said labelled oligonucleotides that hybridised in a) with the target nucleic acid.

c) incubating under hybridisation conditions the recovered labelled oligonucleotides from b) with the array of immobolised oligonucleotides, d) observing distribution of the labelled oligonucleotides on the array and using the information to analyse the target nucleic acid.

2. The method as claimed in claim 1, wherein the target nucleic acid used in a) is immobilised.

3. A method of determining differences between a target nucleic acid and a reference nucleic acid, by the use of a first mixture of oligonucleotides in solution labelled with a first label, a corresponding second mixture of oligonucleotides in solution labelled with a second label distinguishable from the first label, and an array of immobilised oligonucleotides, which method comprises the steps of:

a) incubating under hybridisation conditions the target nucleic acid with the first mixture of labelled oligonucleotides; and incubating under hybridisation conditions the reference nucleic acid with the second mixture of labelled oligonucleotides, b) dissociating and recovering said first labelled oligonucleotides and those second labelled oligonucleotides that hybridised in a) with the target nucleic acid or the reference nucleic acid, c) incubating under hybridisation conditions the recovered mixture of first labelled oligonucleotides and of second labelled oligonucleotides from b) with the array of immobilised oligonucleotides, d) observing distribution of the first labelled oligonucleotides and of the second labelled oligonucleotides on the array and using the information to determine differences between the target nucleic acid and the reference nucleic acid.

4. The method as claimed in claim 3, wherein the target nucleic acid used in a) is immobilised, and the reference nucleic acid used in a) is immobilised.

5. The method as claimed in any one of claims 1 to 4, wherein the mixture or each mixture of labelled oligonucleotides used in a) is a complete set or a subset of all N-mers wherein N is 5 to 10.

6. The method as claimed in any one of claims 1 to 4, wherein the array of immobilised oligonucleotides used in c) is an array of a complete set or a subset of all N-mers wherein N is 5 to 10.

7. The method as claimed in claim 5, wherein N is 8 or 9.

8. The method as claimed in any one of claims 1 to 4, wherein the labelled oligonucleotides in solution are DNA, RNA, PNA, other nucleic acid mimetics or mixtures thereof, are single stranded or partially double stranded, and may comprise residues of one or more nucleotide analogues.

9. The method as claimed in any one of claims 1 to 4, wherein the oligonucleotides of the array are DNA, RNA, PNA, other nucleic acid mimetics or mixtures thereof, are single stranded or partially double stranded, and may comprise residues of one or more nucleotide analogues.

10. The method as claimed in any one of claims 1 to 4, wherein the target nucleic acid is generated by PCR.

11. A kit for performing the method of any one of claims 1 to 4 comprising a supply of a mixture of labelled oligonucleotides in solution and an array of immobilised oligonucleotides.

12. The method as claimed in claim 6, wherein N is 8 or 9.

13. The method as claimed in claim 1 or 3, wherein the labelled oligonucleotides each comprise a different nucleotide sequence.

* * * * *